(12) United States Patent
McGuckin, Jr. et al.

(10) Patent No.: US 7,604,649 B2
(45) Date of Patent: Oct. 20, 2009

(54) DISTAL PROTECTION DEVICE

(75) Inventors: James F. McGuckin, Jr., Radnor, PA (US); Walter H. Peters, Downingtown, PA (US); Peter W. J. Hinchliffe, Campbell Hall, NY (US); Paul Tashjian, King of Prussia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 411 days.

(21) Appl. No.: 10/800,299

(22) Filed: Mar. 12, 2004

(65) Prior Publication Data
US 2005/0004597 A1 Jan. 6, 2005

Related U.S. Application Data

(60) Provisional application No. 60/466,491, filed on Apr. 29, 2003.

(51) Int. Cl.
*A61M 29/00* (2006.01)
(52) U.S. Cl. ..................................................... 606/200
(58) Field of Classification Search ................ 600/200; 606/113, 200; 623/1.11
See application file for complete search history.

(56) References Cited

U.S. PATENT DOCUMENTS

| | | | |
|---|---|---|---|
| 4,425,908 A | 1/1984 | Simon | |
| 4,873,978 A | 10/1989 | Ginsburg | |
| 5,100,423 A * | 3/1992 | Fearnot | 606/159 |
| 5,192,286 A * | 3/1993 | Phan et al. | 606/127 |
| 5,421,832 A * | 6/1995 | Lefebvre | 264/173.11 |
| 5,626,602 A | 5/1997 | Gianotti et al. | |
| 5,658,296 A | 8/1997 | Bates et al. | |
| 5,720,764 A | 2/1998 | Naderlinger | |
| 5,814,064 A * | 9/1998 | Daniel et al. | 606/200 |
| 5,827,324 A | 10/1998 | Cassell et al. | |
| 5,848,964 A | 12/1998 | Samuels | |
| 5,941,896 A | 8/1999 | Kerr | |
| 5,972,019 A | 10/1999 | Engelson et al. | |
| 5,984,947 A * | 11/1999 | Smith | 606/200 |
| 6,001,118 A | 12/1999 | Daniel et al. | |
| 6,027,520 A | 2/2000 | Tsugita et al. | |
| 6,056,770 A | 5/2000 | Epstein et al. | |
| 6,066,149 A | 5/2000 | Samson et al. | |
| 6,066,158 A | 5/2000 | Engelson et al. | |
| 6,080,178 A * | 6/2000 | Meglin | 606/200 |
| 6,096,053 A | 8/2000 | Bates | |
| 6,123,715 A | 9/2000 | Amplatz | |
| 6,129,739 A * | 10/2000 | Khosravi | 606/200 |
| 6,146,396 A | 11/2000 | Kónya et al. | |

(Continued)

FOREIGN PATENT DOCUMENTS

WO    WO 9601591    1/1996

(Continued)

*Primary Examiner*—Darwin P Erezo
(74) *Attorney, Agent, or Firm*—Neil D. Gershon

(57) ABSTRACT

A distal protection device comprising a catheter, a flexible member movable from a first position to a second looped position extending laterally with respect to the catheter, such that a first loop opening extends substantially in a direction of blood flow as the first loop opening extends in a plane substantially parallel to a transverse axis of the catheter, and filtering material movable from a collapsed position to an expanded position in response to movement of the flexible member.

14 Claims, 18 Drawing Sheets

U.S. PATENT DOCUMENTS

| | | | |
|---|---|---|---|
| 6,152,946 A | 11/2000 | Broome et al. |
| 6,168,579 B1 | 1/2001 | Tsugita |
| 6,171,327 B1 | 1/2001 | Daniel et al. |
| 6,179,851 B1 | 1/2001 | Barbut et al. |
| 6,179,861 B1 | 1/2001 | Khosravi et al. |
| 6,187,025 B1 | 2/2001 | Machek |
| 6,224,620 B1 | 5/2001 | Maahs |
| 6,245,088 B1 | 6/2001 | Lowery |
| 6,258,115 B1 | 7/2001 | Dubrul |
| 6,264,672 B1 | 7/2001 | Fisher |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,338,735 B1 | 1/2002 | Stevens |
| 6,340,364 B2 * | 1/2002 | Kanesaka ............... 606/200 |
| 6,346,116 B1 | 2/2002 | Brooks et al. |
| 6,348,056 B1 | 2/2002 | Bates et al. |
| 6,364,895 B1 | 4/2002 | Greenhalgh |
| 6,364,900 B1 | 4/2002 | Heuser |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,425,909 B1 * | 7/2002 | Dieck et al. ............... 606/200 |
| 6,482,222 B1 | 11/2002 | Bruckheimer et al. |
| 6,485,501 B1 | 11/2002 | Green |
| 6,500,191 B2 | 12/2002 | Addis |
| 6,530,939 B1 | 3/2003 | Hopkins et al. |
| 6,544,279 B1 | 4/2003 | Hopkins et al. |
| 6,551,268 B1 | 4/2003 | Kaganov et al. |
| 6,558,405 B1 | 5/2003 | McInnes |
| 6,562,058 B2 | 5/2003 | Seguin et al. |
| 6,569,184 B2 | 5/2003 | Huter |
| 6,582,448 B1 | 6/2003 | Boyle et al. |
| 6,589,263 B1 | 7/2003 | Hopkins et al. |
| 6,592,606 B2 | 7/2003 | Huter et al. |
| 6,592,616 B1 | 7/2003 | Stack et al. |
| 6,596,011 B2 | 7/2003 | Johnson et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,616,680 B1 | 9/2003 | Thielen |
| 6,620,182 B1 | 9/2003 | Khosravi et al. |
| 6,635,068 B1 | 10/2003 | Dubrul et al. |
| 6,635,070 B2 | 10/2003 | Leeflang et al. |
| 6,638,294 B1 | 10/2003 | Palmer |
| 6,645,220 B1 | 11/2003 | Huter et al. |
| 6,645,223 B2 | 11/2003 | Boyle et al. |
| 6,652,505 B1 | 11/2003 | Tsugita |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,207 B2 | 12/2003 | Epstein et al. |
| 6,660,021 B1 | 12/2003 | Palmer et al. |
| 6,663,652 B2 | 12/2003 | Daniel et al. |
| 6,695,813 B1 | 2/2004 | Boyle et al. |
| 6,695,865 B2 | 2/2004 | Boyle et al. |
| 6,706,053 B1 | 3/2004 | Boylan et al. |
| 6,706,055 B2 | 3/2004 | Douk et al. |
| 6,716,231 B1 | 4/2004 | Rafiee et al. |
| 6,726,701 B2 * | 4/2004 | Gilson et al. ............... 606/200 |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,755,847 B2 | 6/2004 | Eskuri |
| 6,761,727 B1 | 7/2004 | Ladd |
| 6,761,732 B2 | 7/2004 | Burkett et al. |
| 6,773,448 B2 | 8/2004 | Kusleika et al. |
| 6,818,006 B2 | 11/2004 | Douk et al. |
| 6,837,898 B2 | 1/2005 | Boyle et al. |
| 6,840,950 B2 | 1/2005 | Stanford et al. |
| 6,911,036 B2 | 6/2005 | Douk et al. |
| 6,918,921 B2 | 7/2005 | Brady et al. |
| 6,929,652 B1 | 8/2005 | Andrews et al. |
| 6,936,059 B2 | 8/2005 | Belef |
| 7,331,976 B2 * | 2/2008 | McGuckin et al. ............ 606/200 |
| 2001/0011182 A1 | 8/2001 | Dubrul et al. |
| 2002/0095171 A1 | 7/2002 | Belef |
| 2002/0183783 A1 | 12/2002 | Shadduck |
| 2003/0004540 A1 | 1/2003 | Linder et al. |
| 2003/0004541 A1 | 1/2003 | Linder et al. |
| 2003/0045898 A1 | 3/2003 | Harrison et al. |
| 2003/0060844 A1 | 3/2003 | Borillo et al. |
| 2003/0065355 A1 | 4/2003 | Weber |
| 2003/0100917 A1 | 5/2003 | Boyle et al. |
| 2003/0100918 A1 | 5/2003 | Duane |
| 2003/0114880 A1 | 6/2003 | Hansen et al. |
| 2004/0049223 A1 | 3/2004 | Nishtala et al. |
| 2005/0101988 A1 | 5/2005 | Stanford et al. |
| 2005/0177187 A1 | 8/2005 | Gray et al. |
| 2005/0216052 A1 | 9/2005 | Mazzocchi et al. |

FOREIGN PATENT DOCUMENTS

| | | |
|---|---|---|
| WO | WO 0007521 | 2/2000 |
| WO | WO 0007655 | 2/2000 |
| WO | WO 0145590 | 6/2001 |

* cited by examiner

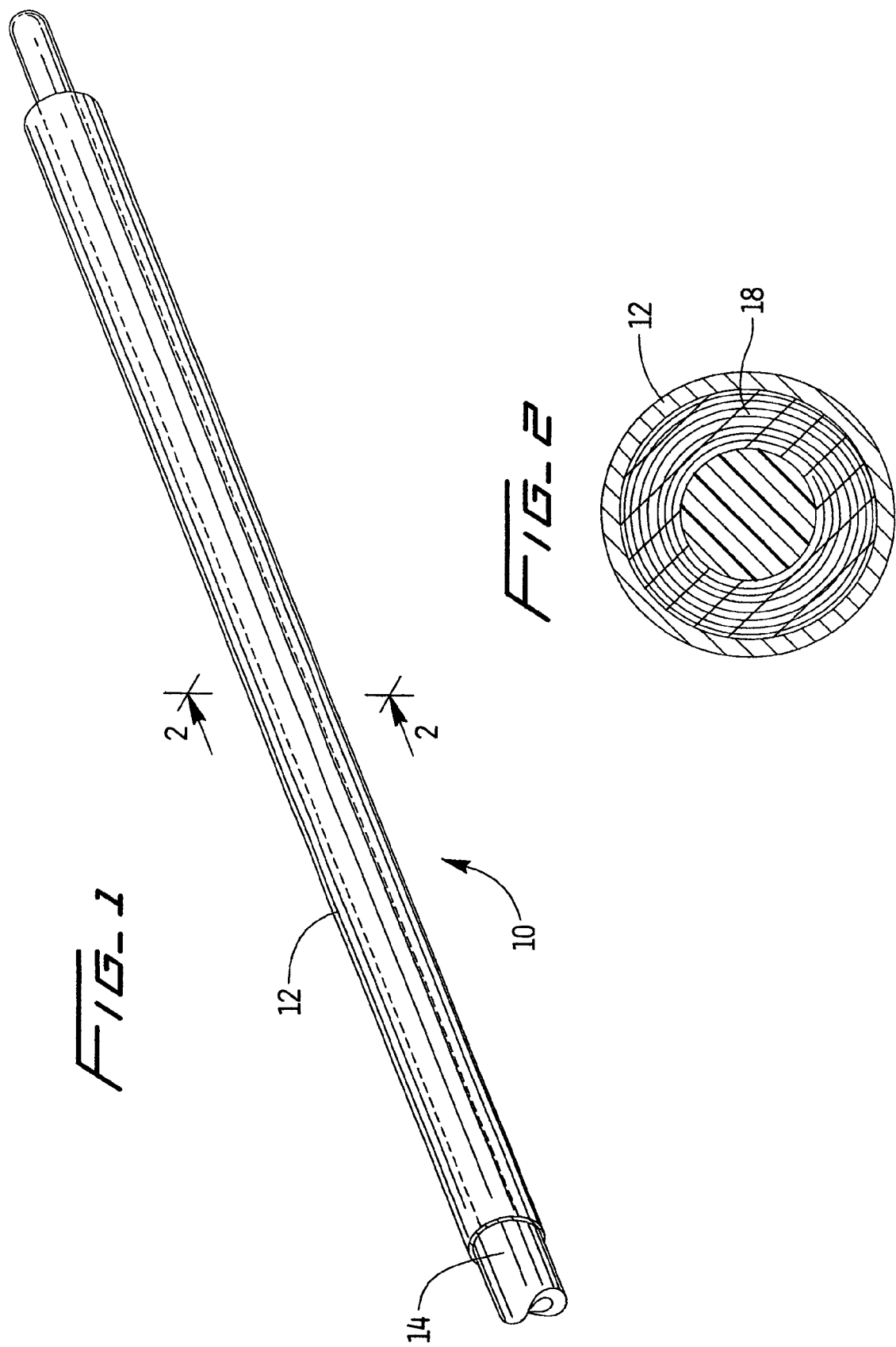

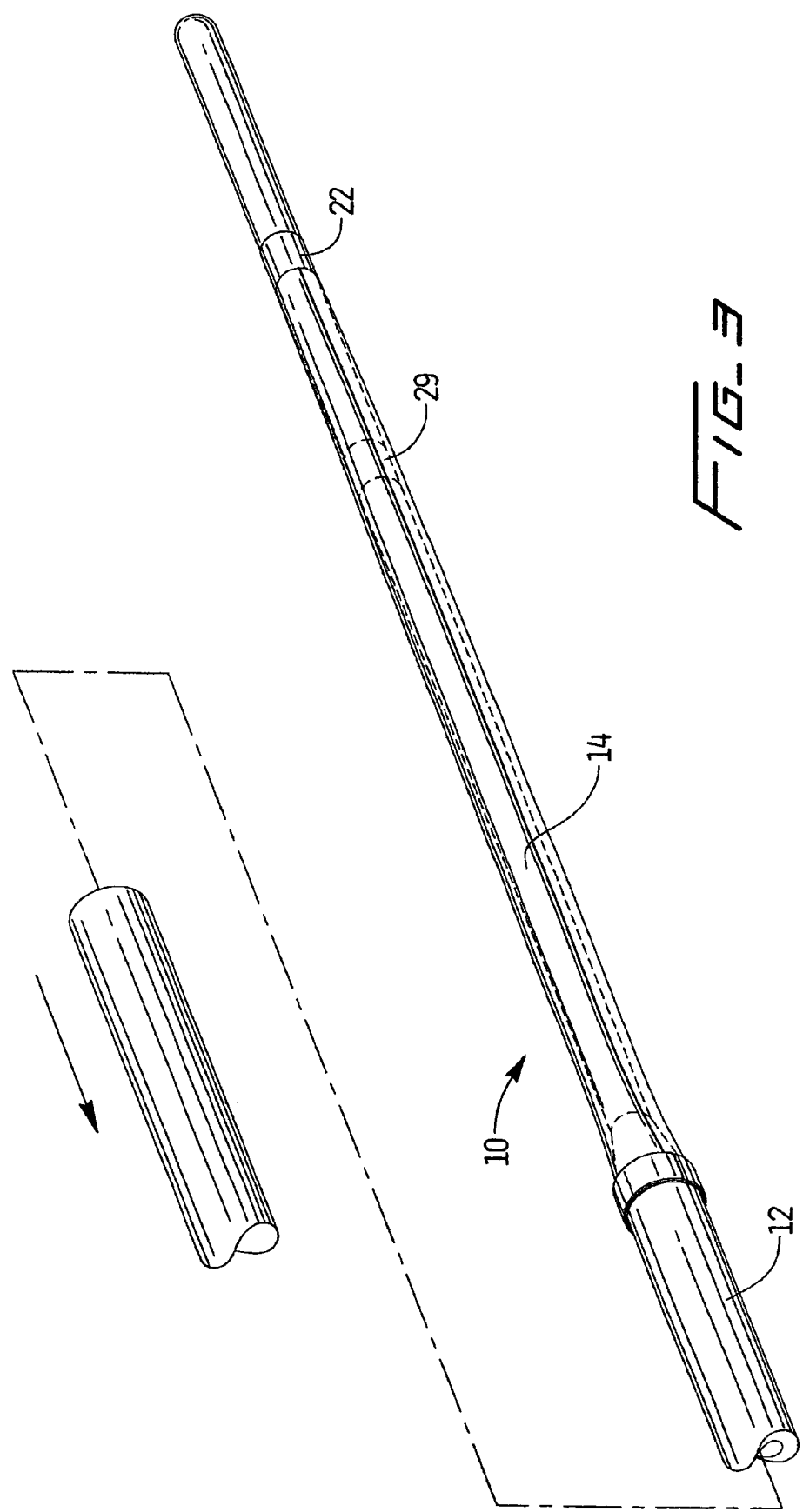

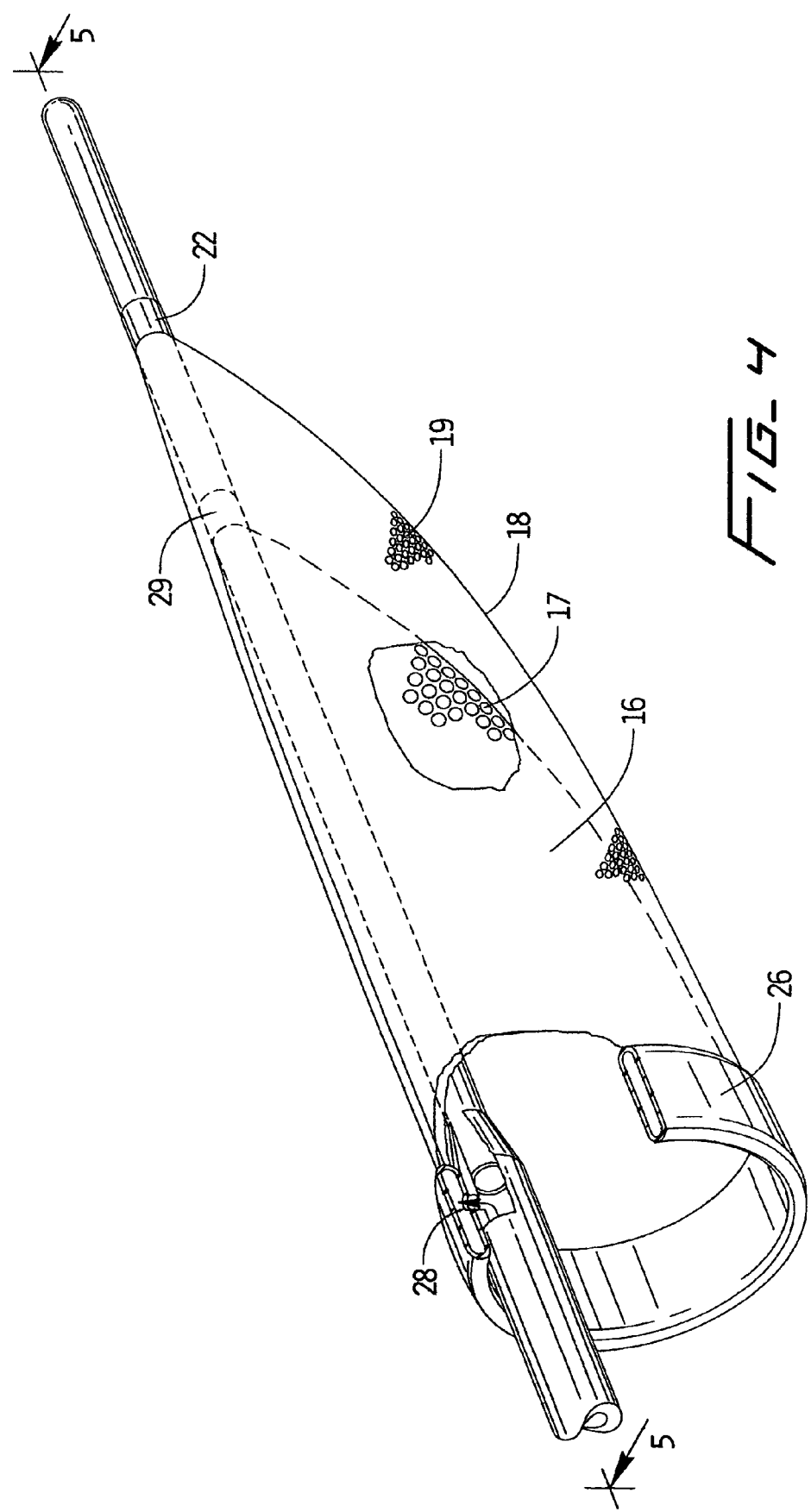

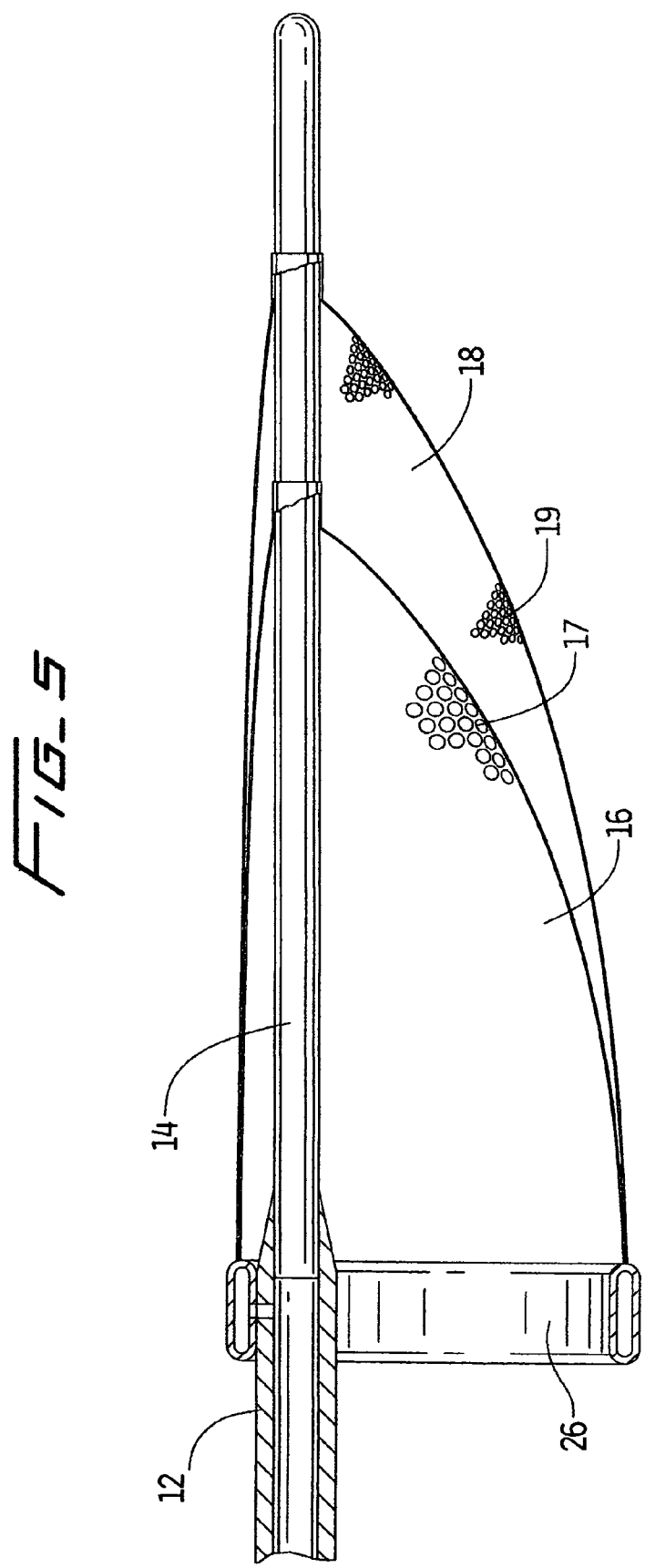

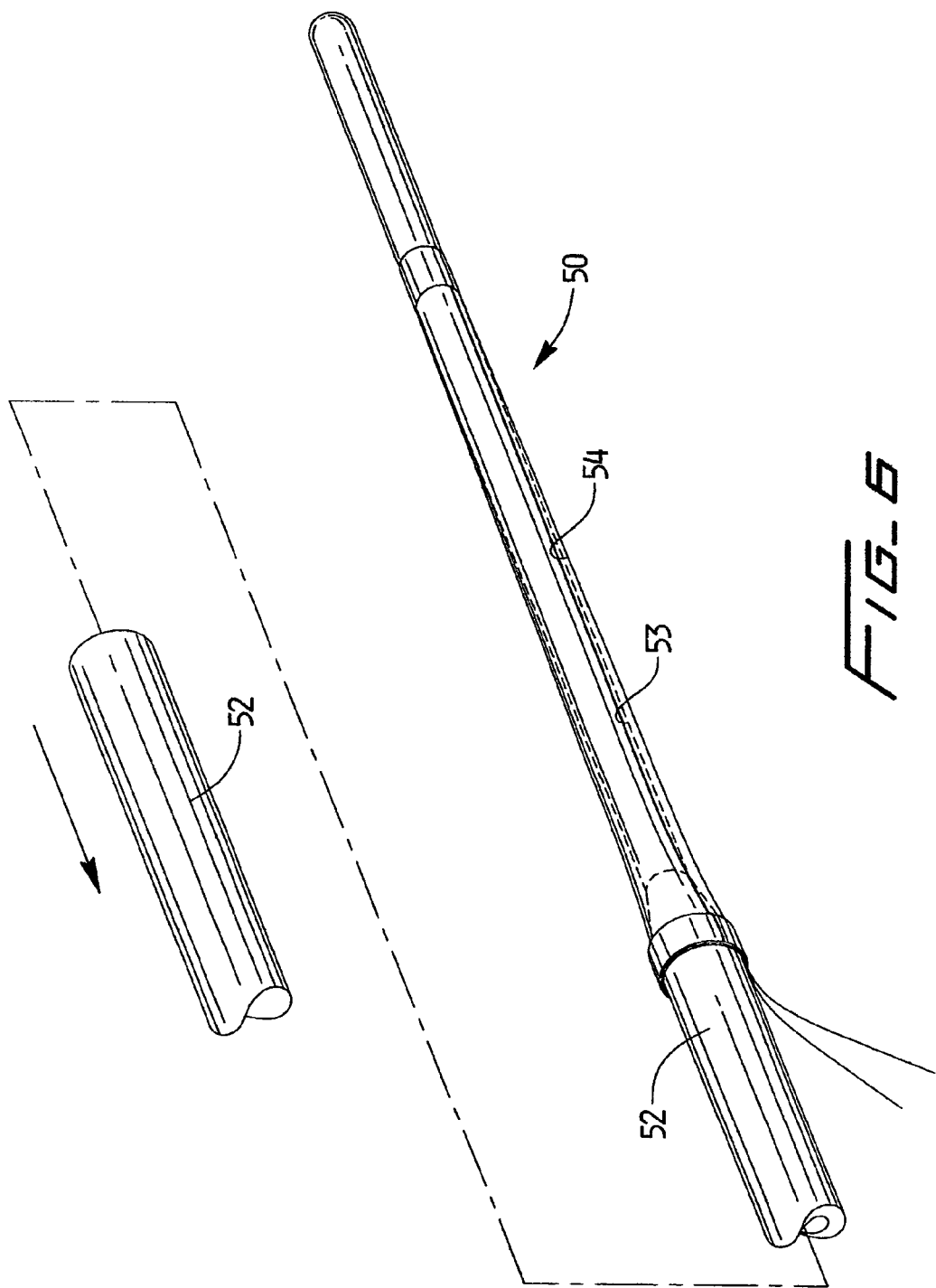

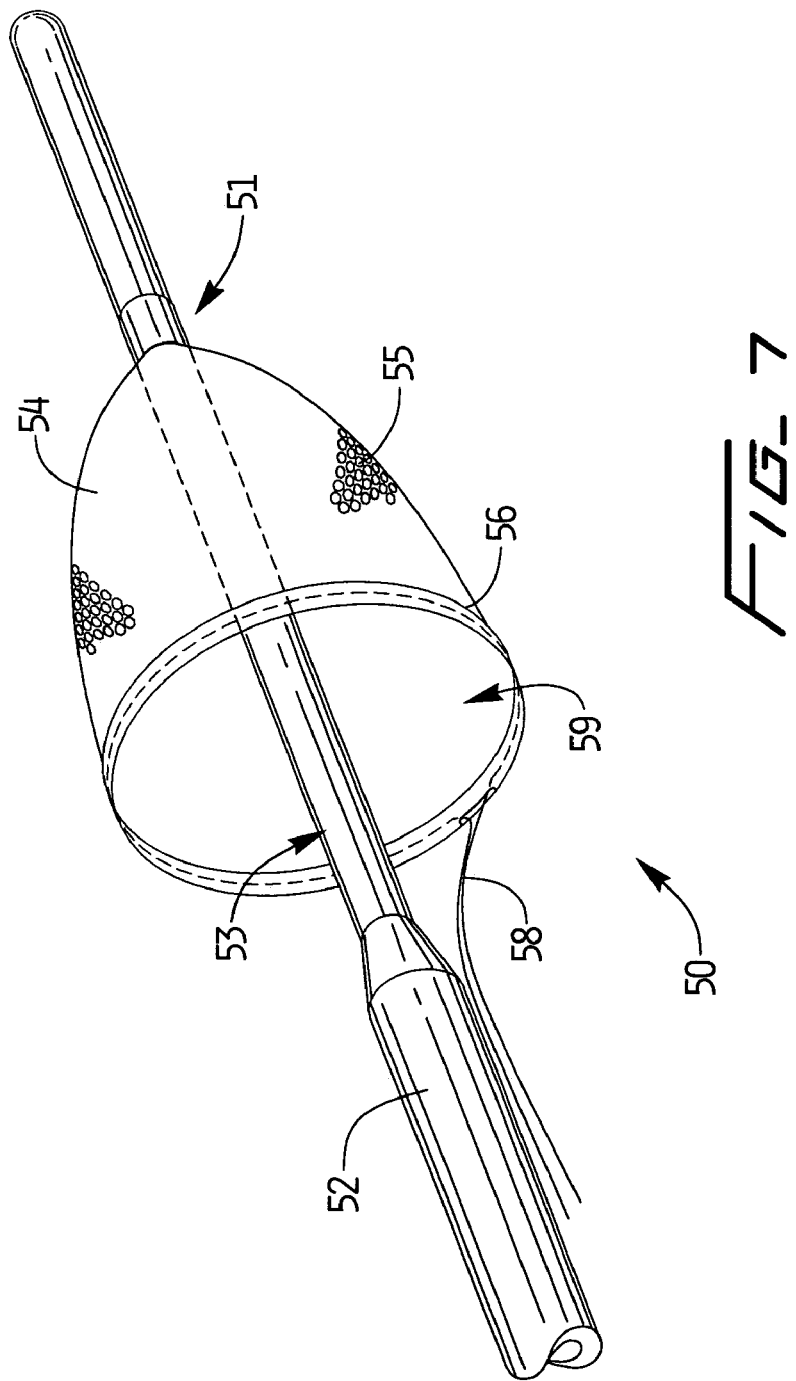

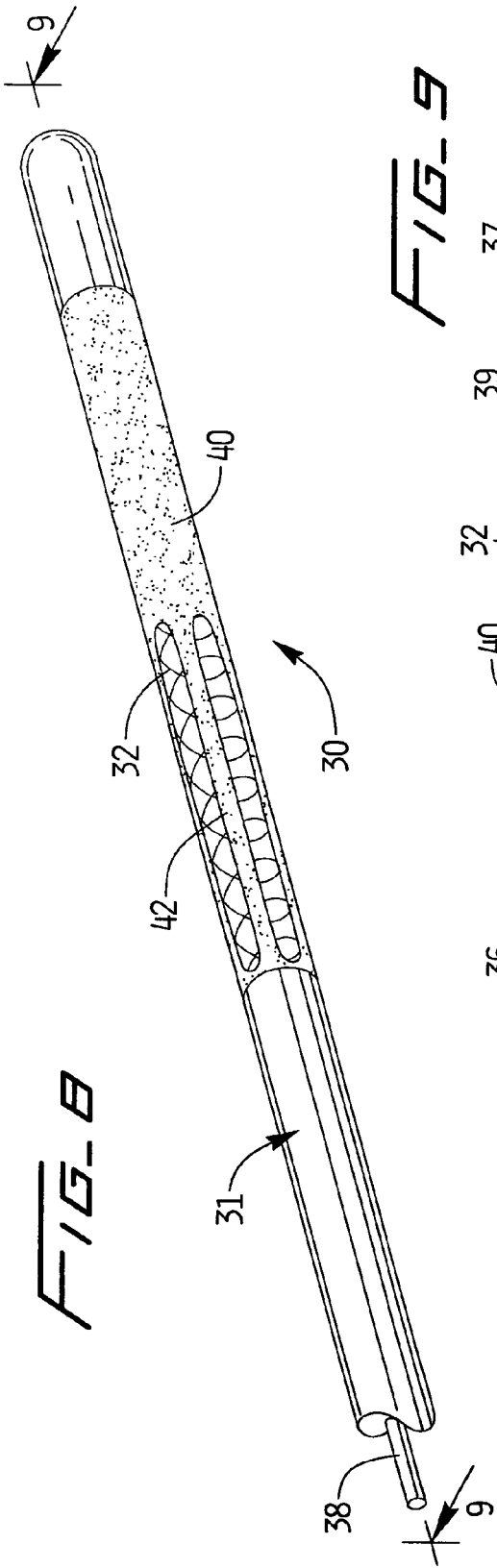
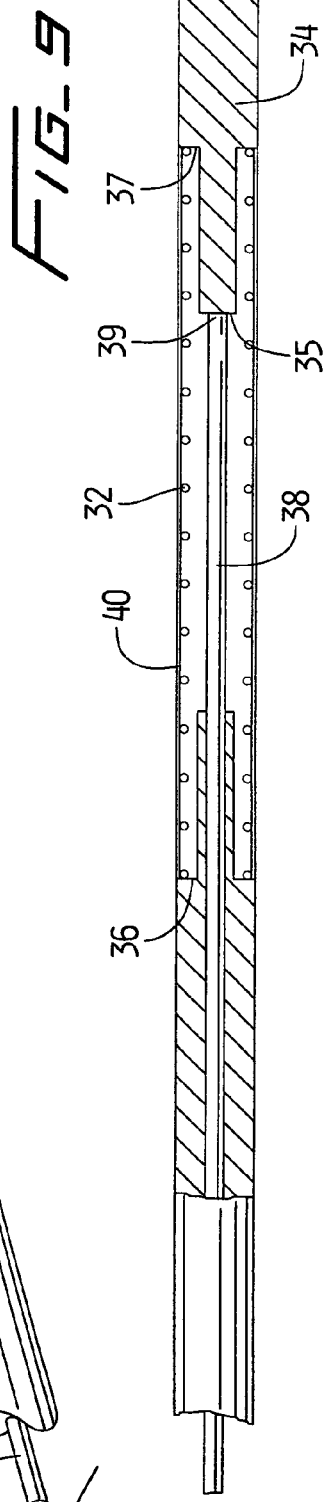
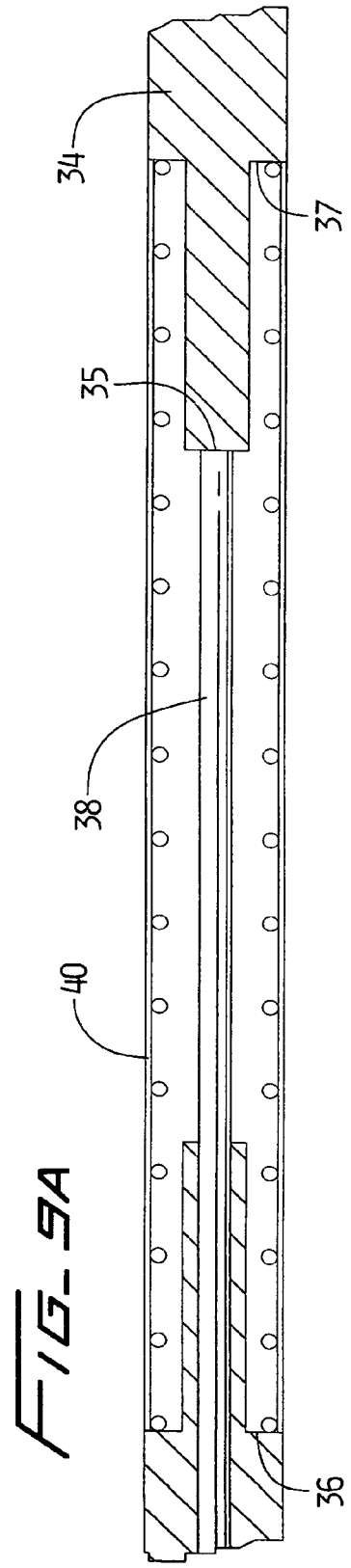

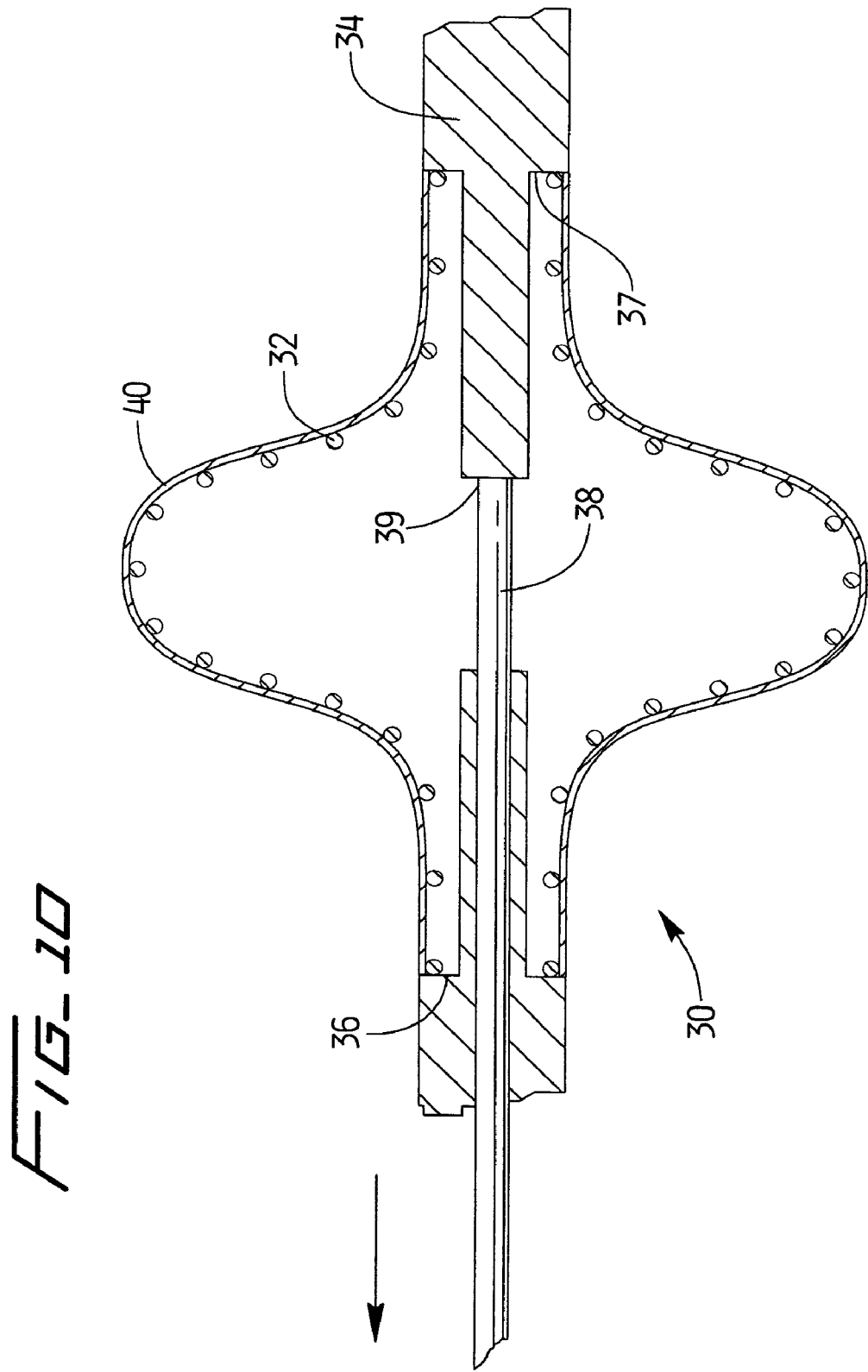

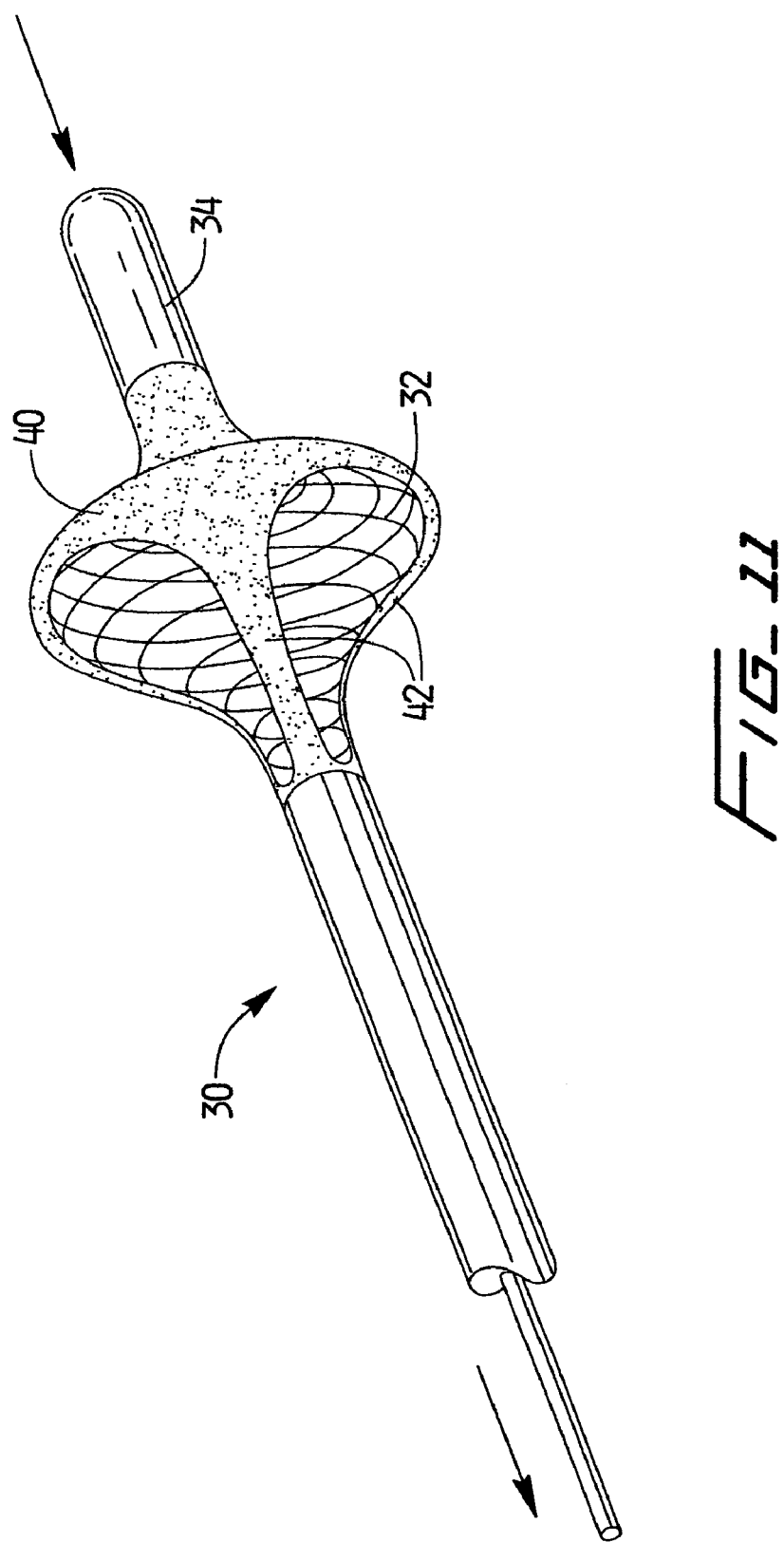
FIG_11

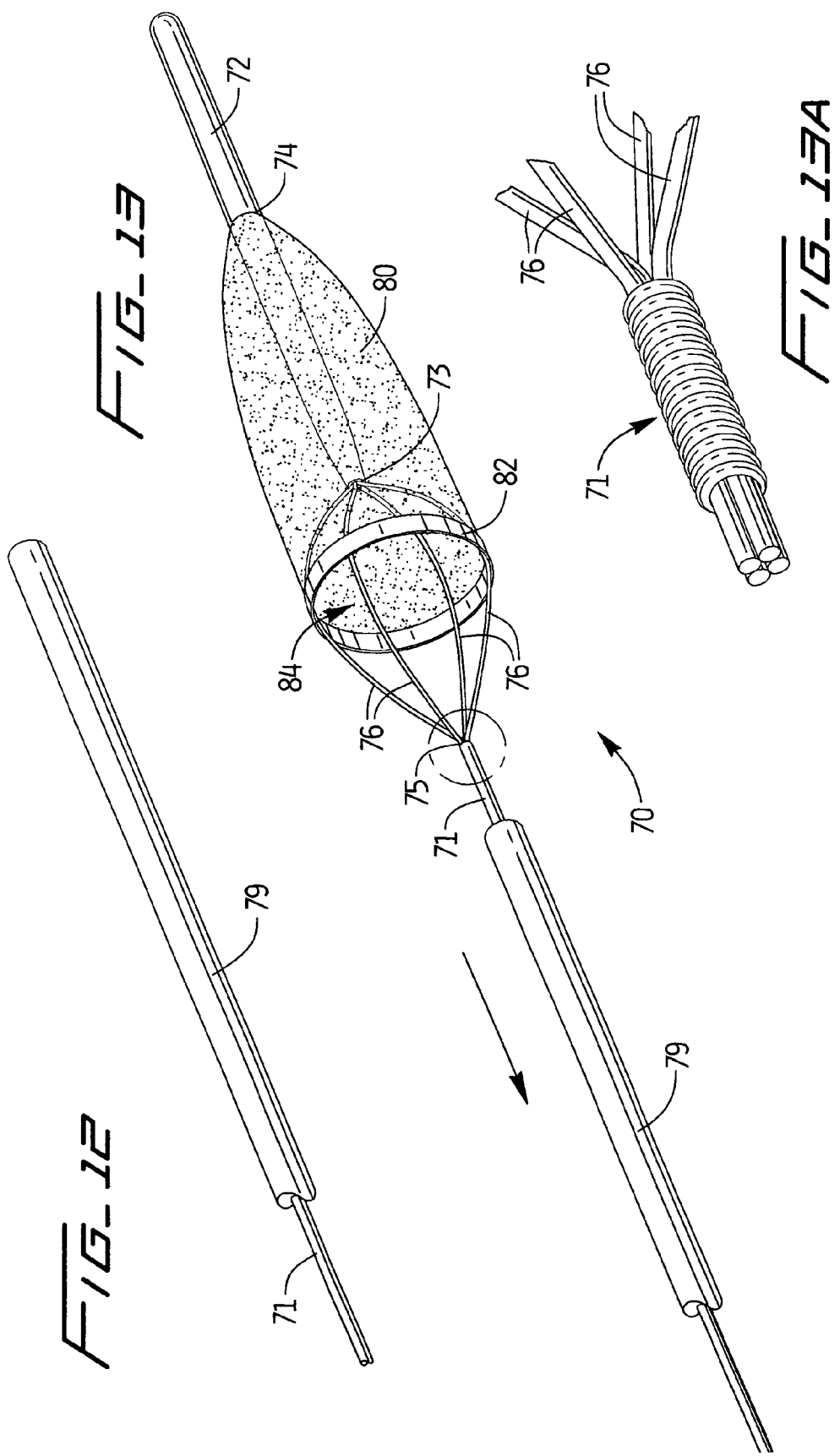

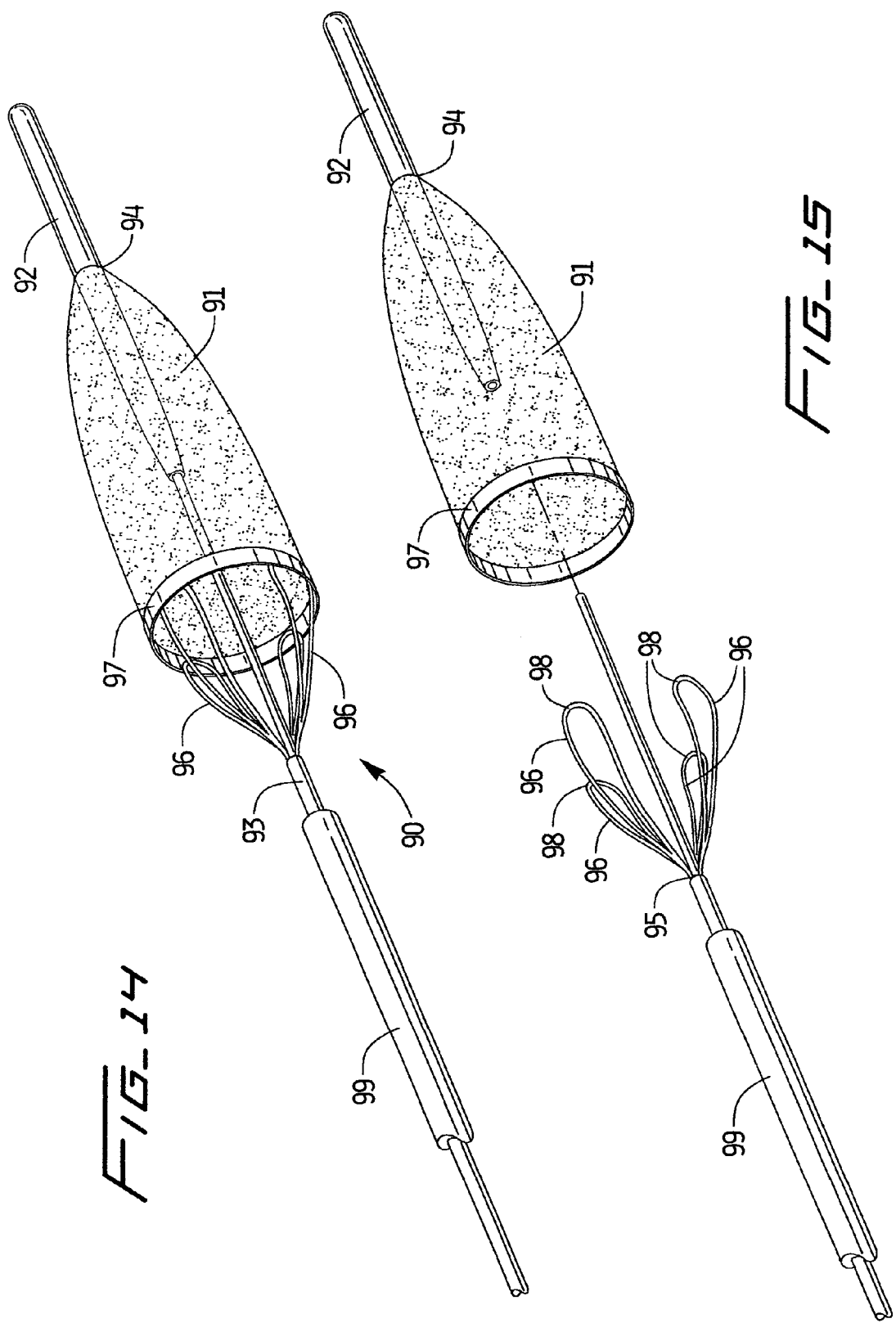

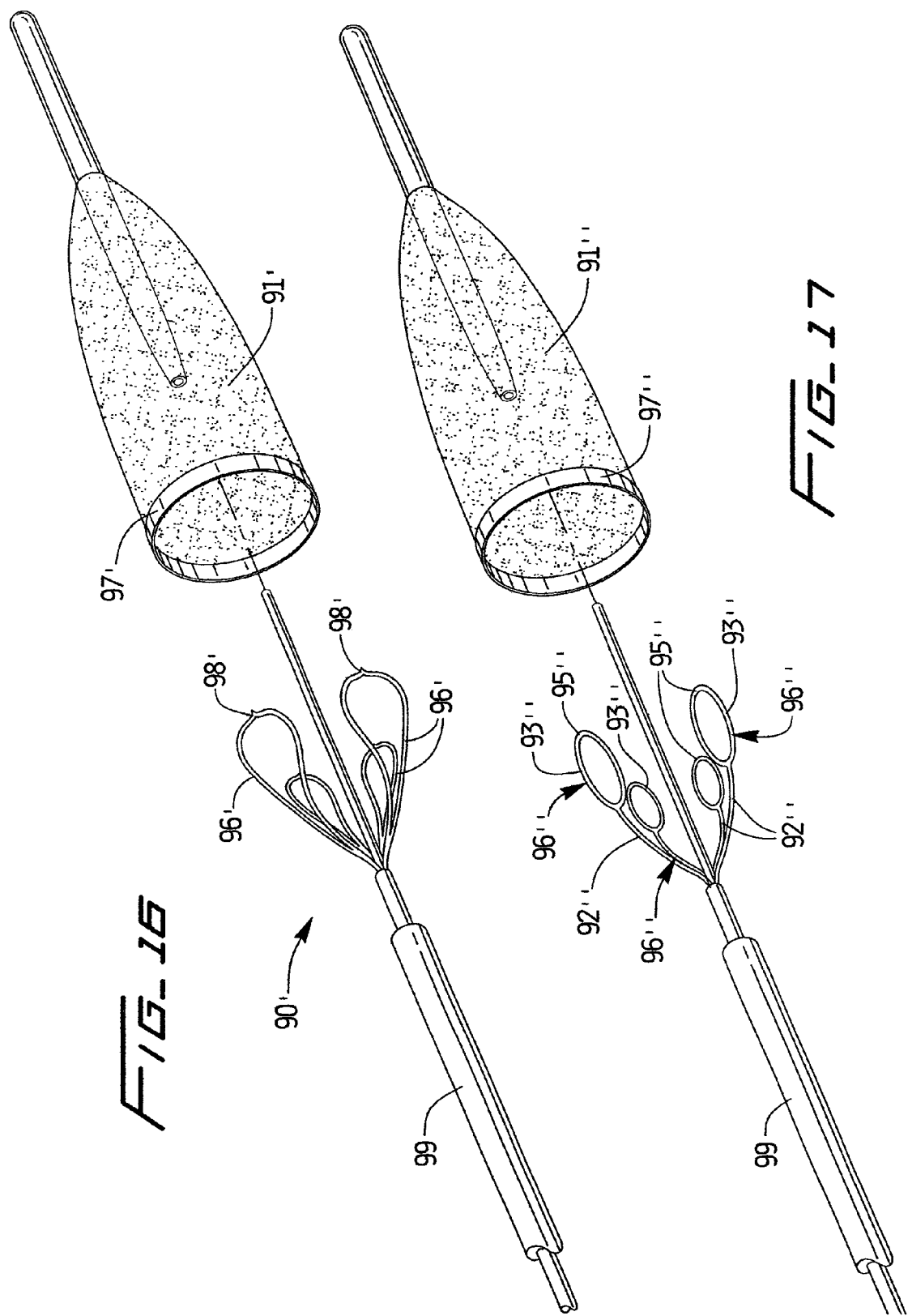

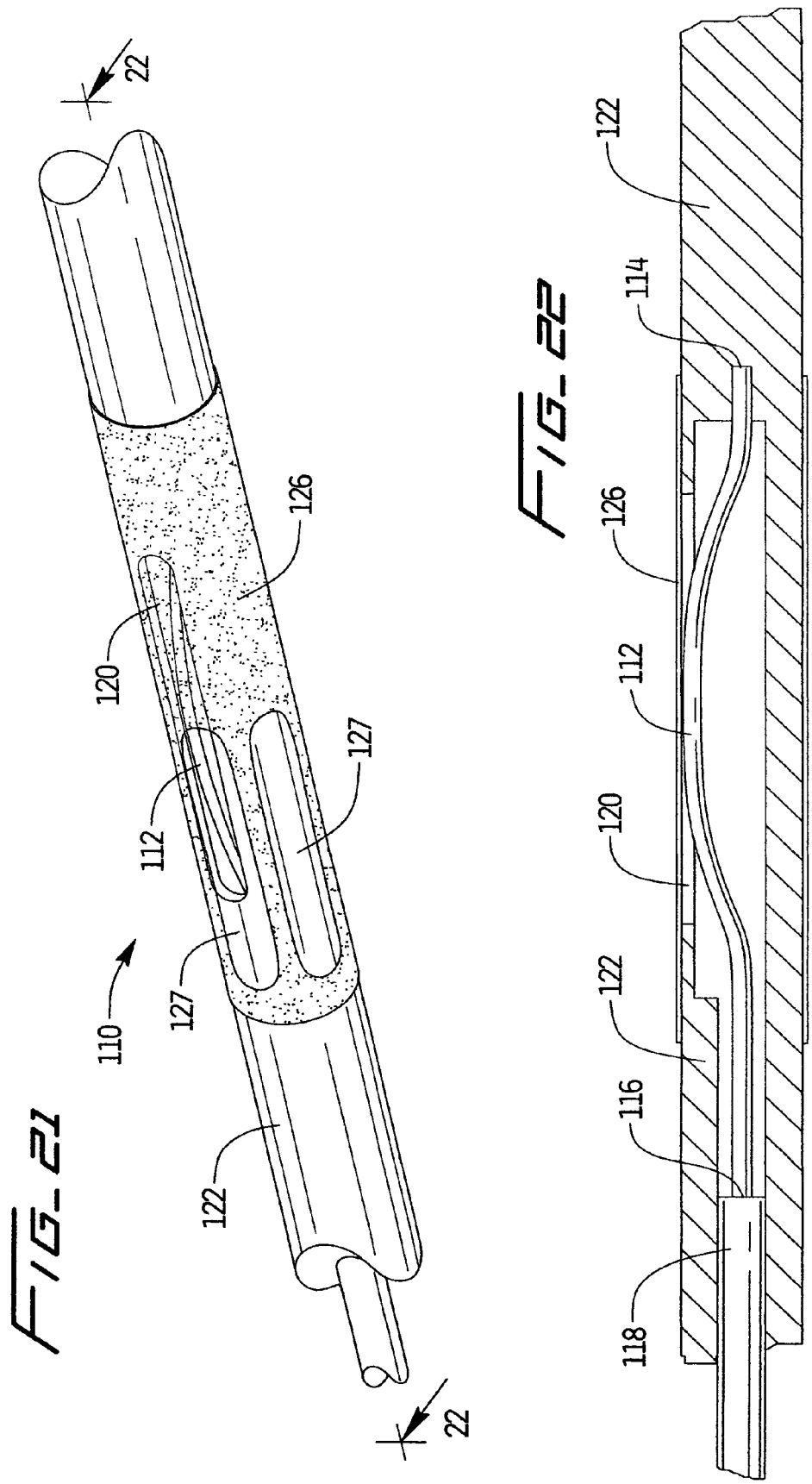

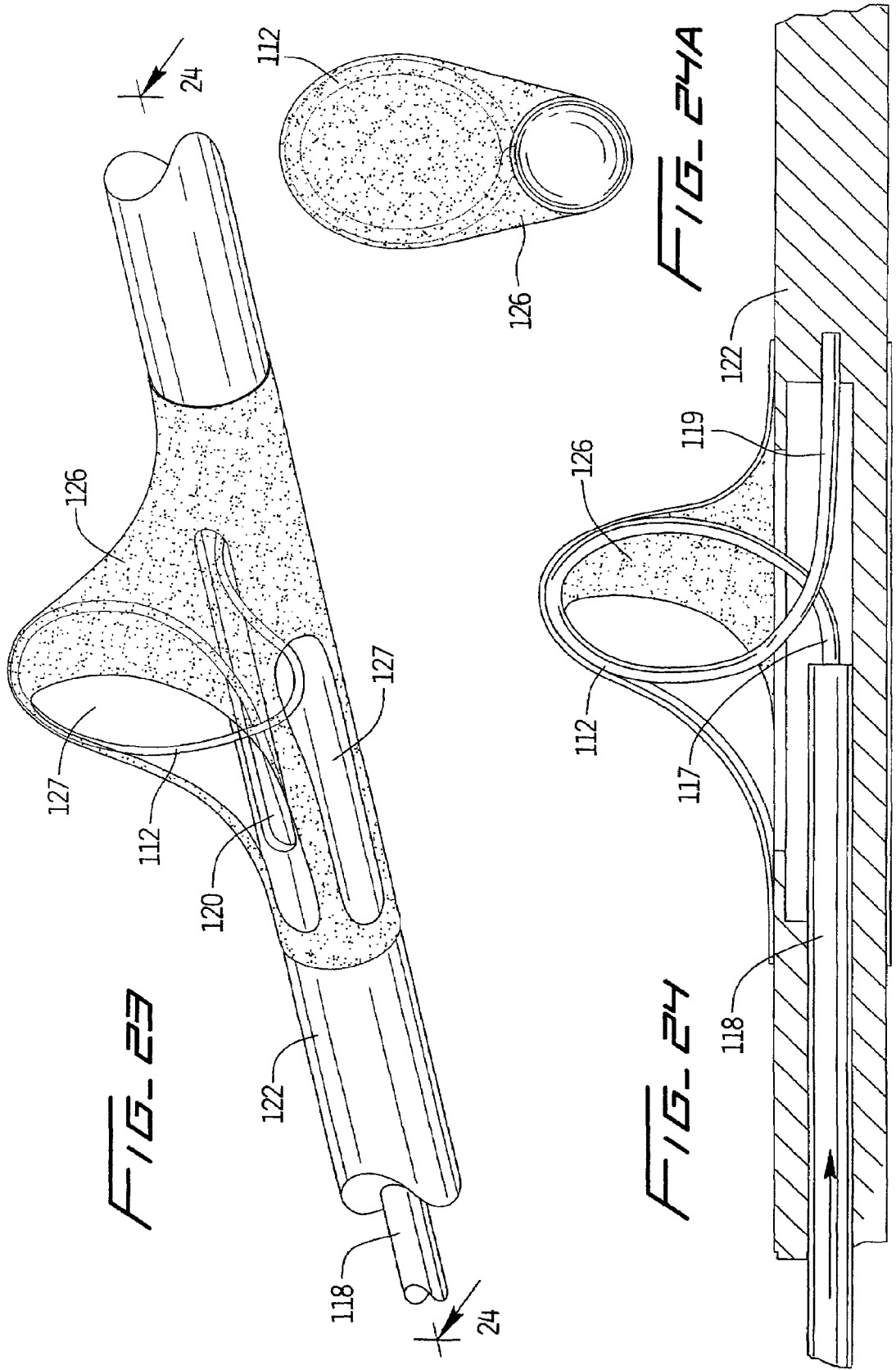

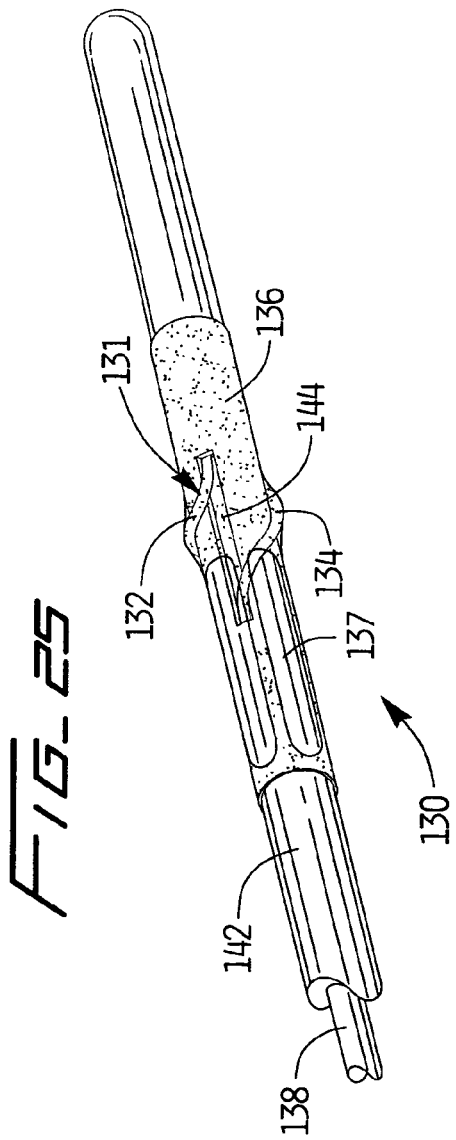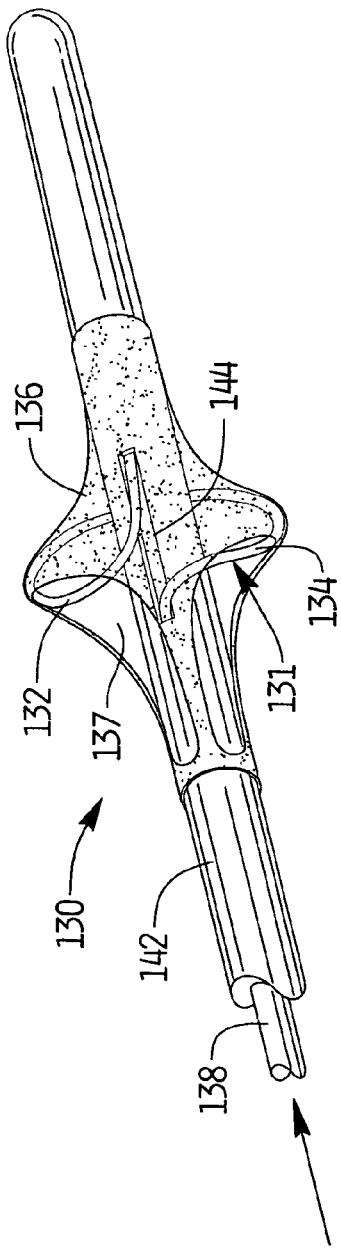

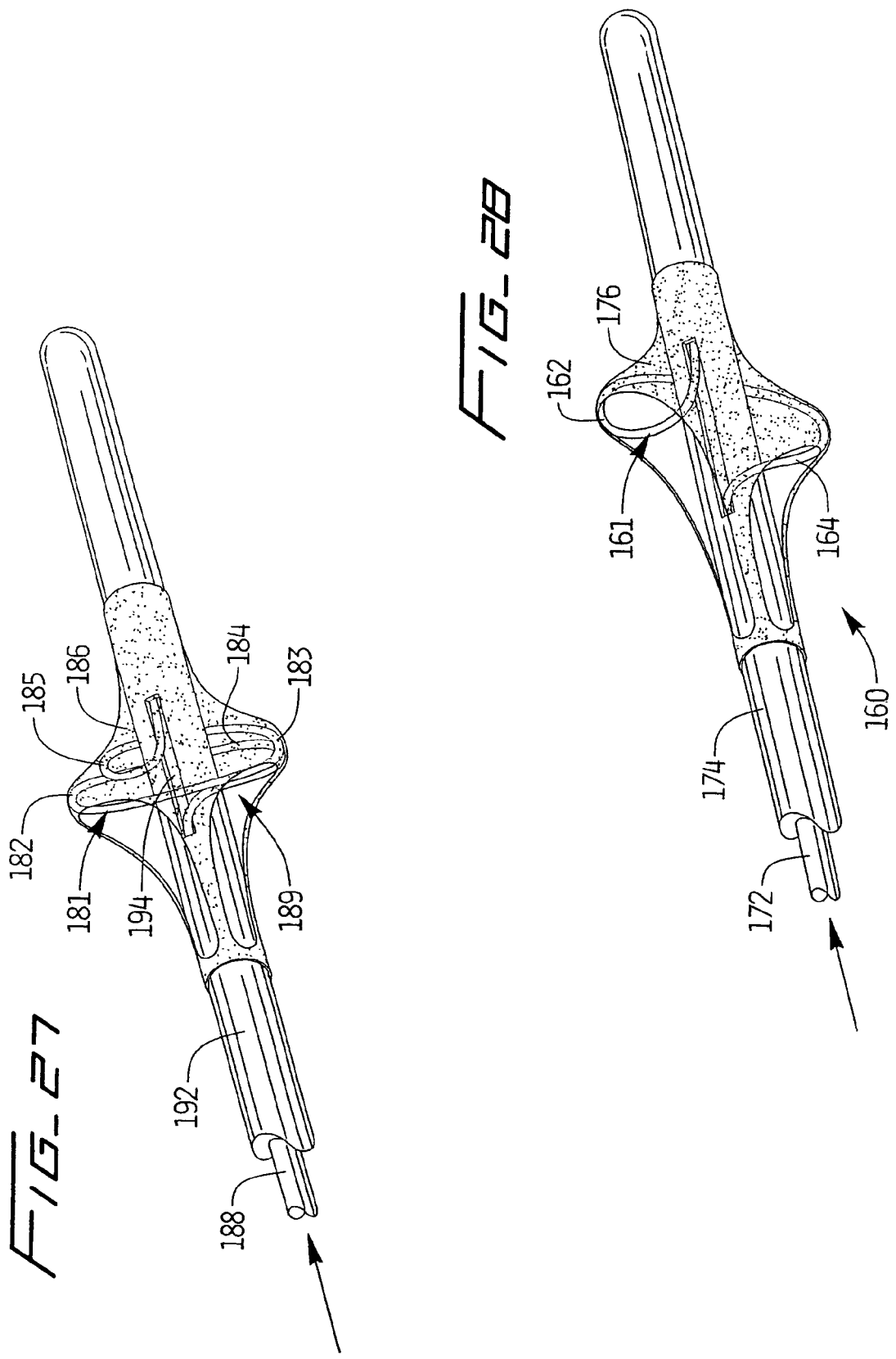

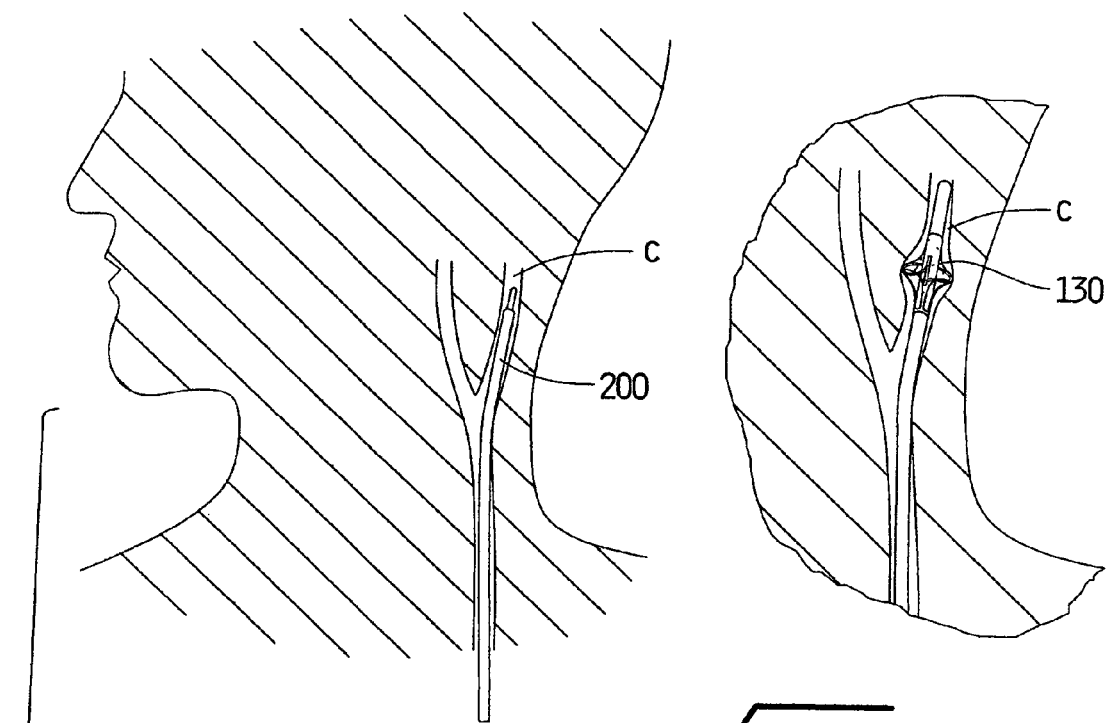
FIG_29
FIG_29A
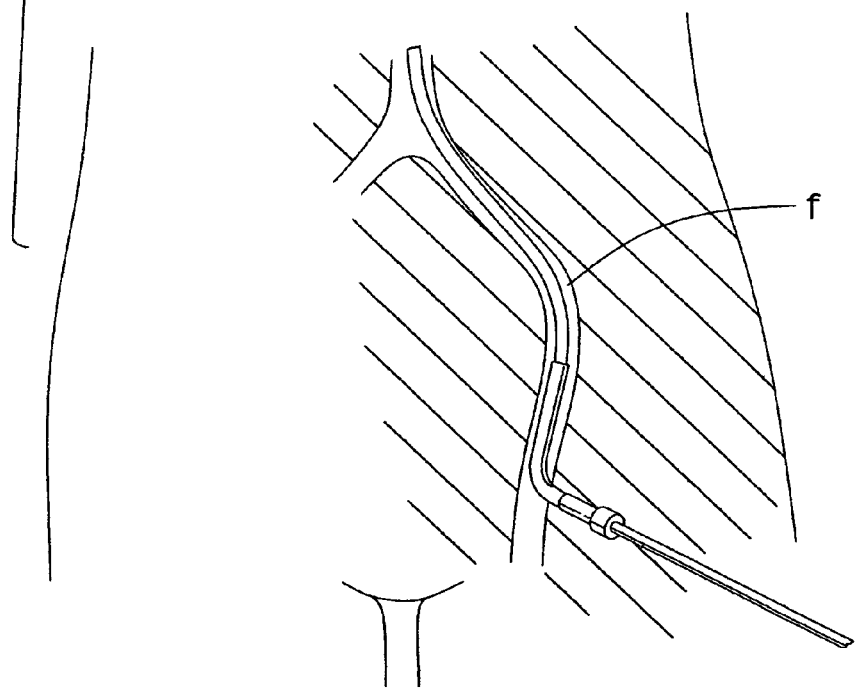

DISTAL PROTECTION DEVICE

This application claims priority from provisional application Ser. No. 60/466,491, filed Apr. 29, 2003, the entire contents of which is incorporated herein by reference.

BACKGROUND

1. Technical Field

This application relates to a vascular device and more particularly to a vascular device for capturing embolic material during surgical procedures.

2. Background of Related Art

During vascular surgical procedures such as stenting, angioplasty, thrombectomy, and atherectomy, embolic material such as plaque and blood clots can become dislodged. Dislodgement of such embolic material can cause the emboli to flow downstream to lodge in the vascular system, thereby occluding flow of oxygenated blood to the brain or other vital organs. Such occlusion can compromise peripheral circulation or result in heart attack, stroke or even death.

Techniques to cut the debris into smaller sizes, such as by use of lasers, have had significant drawbacks, such as the inability to ensure all the debris is cut into sufficiently small fragments. If some of the fragments remain too large, then occlusion of the vessels can occur causing the problems and risks enumerated above.

Attempts have been made to place a device distal (downstream) of the stenosis, thrombus, etc. to capture the emboli. Such distal protection devices typically are collapsible for insertion and expandable once in the vessel. Some devices are in the form of an expandable balloon which is inserted within the vessel inside a sheath. When the sheath is withdrawn, the balloon is expanded to block emboli. These balloon devices even in the collapsed position increase the profile of the device since they are wrapped on the outside of the device. In other distal protection devices, a wire is covered by a membrane. These wires extend laterally from the device and may not enable the membrane to block the entire region of the vessel. Failure to expand to geometry to block the entire region can result in the unwanted passage of debris which can cause vessel occlusion and the aforementioned adverse consequences.

The need therefore exists for an improved distal protection device. Such device would have a reduced profile to facilitate insertion and to better enable placement of the device distal of the emboli to block potential downstream flow. The device would also be easy to manipulate and sufficiently fill the vessel area to ensure all passage is blocked.

SUMMARY

The present invention overcomes the problems and deficiencies of the prior art. The present invention provides a distal protection device comprising a catheter and a flexible member movable from a first retracted position to a second looped position extending laterally with respect to the catheter such that a first loop opening extends substantially in a direction of blood flow as the first loop opening lies in a plane substantially parallel to a transverse axis of the catheter. Filtering material is movable from a collapsed position to a deployed position in response to movement of the flexible member.

In one embodiment, the flexible member is contained within the catheter in the first position so the cross sectional dimension of the catheter at a portion containing the flexible member does not exceed other cross-sectional dimensions of the catheter. In one embodiment, the flexible member extends through a sidewall in the catheter.

In one embodiment, a second loop is spaced from the first loop and movable from a first position to a second looped position extending laterally from the sidewall of the catheter. Preferably the loops extend in opposite directions with respect to the catheter so in the second looped position the loops are approximately 180 degrees apart. In one embodiment of the multiple loop configuration, the loops are axially offset.

The present invention also provides a distal protection device comprising a catheter having an opening in a sidewall, a flexible wire positioned within the catheter and movable from a first position having a lower profile for insertion of the catheter to a second position extending laterally from the catheter. In the second position, the wire forms a loop extending laterally such that a first end of the wire extends in a proximal direction and a second end of the wire extends in a distal direction, with the loop therebetween having an opening in a proximal to distal direction. Filtering material is disposed over at least a portion of the wire and movable from a collapsed position to a deployed position in response to movement of the wire.

Preferably on opening of the wire loop is positioned at an angle to a transverse axis and a longitudinal axis of the catheter. In one embodiment the wire forms a second loop in the second position.

The distal protection device may also include an actuating member for moving the wire between the first and second looped positions.

The present invention also provides a distal protection device comprising a catheter and a flexible member movable from a first position to a second looped position extending laterally with respect the catheter such that in the second looped position a loop opening is formed lying in a plane that is non-aligned with a longitudinal axis of the catheter. The flexible member is movable between the first and second positions by user control. Filtering material is provided and movable from a collapsed position to a deployed position in response to movement of the flexible member, wherein the filtering material automatically moves from the deployed position to the collapsed position upon movement of the flexible member back to the first position.

The present invention also provides a distal protection device comprising an outer tube, an inner core, a first inner filter having a series of openings of a first dimension and a second outer filter having a series of openings of a second dimension smaller than the first dimension. At least a portion of the outer filter is positioned external of at least a portion of the inner filter. The device may include a ring positioned on a proximal end of the outer filter.

BRIEF DESCRIPTION OF THE DRAWINGS

Preferred embodiment(s) of the present disclosure are described herein with reference to the drawings wherein:

FIGS. 1-5 illustrate a first embodiment of the distal protection device of the present invention, wherein FIG. 1 is a perspective view;

FIG. 2 is a cross-sectional view taken along lines 2-2 of FIG. 1;

FIG. 3 is a perspective view showing the outer tube withdrawn to enable expansion of the balloons;

FIG. 4 is a perspective view illustrating the inner and outer balloons in the expanded configuration; and FIG. 5 is a side view in partial cross section showing the balloons expanded;

FIG. 6 is a perspective view of a second embodiment of the distal protection device of the present invention having a self-expanding umbrella device;

FIG. 7 is a perspective view of the device of FIG. 6 showing the umbrella device expanded by blood flow;

FIGS. 8 and 9 are perspective and longitudinal cross-sectional views, respectively, of a third embodiment of the distal protection device of the present invention having a membrane formed over a coiled wire, the membrane and wire shown in the retracted insertion position;

FIG. 9A is an enlarged longitudinal cross-sectional view of a portion of the catheter of FIG. 9;

FIG. 10 is a view similar to FIG. 9A except showing the wire and membrane in the expanded position;

FIG. 11 is a perspective view of the device in the expanded position of FIG. 10;

FIGS. 12 and 13 are perspective views of a fourth embodiment of the distal protection device having a membrane fused to a shape memory wire, wherein FIG. 12 shows the shape memory wire and membrane contained within the catheter and FIG. 13 shows the shape memory wire advanced from the catheter to open the membrane to an expanded position;

FIG. 13A is an enlarged view of the area of detail of FIG. 13;

FIGS. 14-17 illustrate three alternate embodiments of the device of FIG. 12, showing varying shape memory wire configurations fused to a membrane wherein;

FIGS. 14 and 15 are perspective views showing looped wires, with FIG. 14 showing the attachment to the membrane ring and FIG. 15 showing an exploded view;

FIG. 16 is an exploded view showing looped wires with pointed bend points; and

FIG. 17 is an exploded view showing individual wire segments terminating in rings;

FIGS. 21 and 22 are respectively perspective and longitudinal cross-sectional views (taken along lines 22-22) of another alternate embodiment of the distal protection device having a single wire loop for deploying the membrane, the membrane and wire shown in the non-expanded (collapsed) position;

FIGS. 23 and 24 are respectively perspective and longitudinal cross-sectional views (taken along lines 24-24) similar to FIGS. 21 and 22 except illustrating the wire in the looped position and membrane in the deployed position;

FIG. 24A is an end view of the device of FIG. 23;

FIGS. 25 and 26 are perspective views of yet another alternate embodiment of the distal protection device of FIG. 21 having a double looped wire for deploying the membrane, the membrane shown in the non-expanded position in FIG. 25 and the deployed position in FIG. 26;

FIG. 27 is a perspective view illustrating another alternate embodiment of the distal protection device of FIG. 21 having multiple wire loops, the membrane shown in the deployed position;

FIG. 28 is a perspective view of an alternate embodiment of the distal protection device of FIG. 26 wherein the wire loops are axially offset; and FIGS. 29 and 29A illustrate placement of the device of FIG. 26, wherein FIG. 29 shows the catheter advanced through the femoral to the carotid artery and FIG. 29A shows the device deployed in the carotid artery to block distal flow of emboli.

DETAILED DESCRIPTION OF PREFERRED EMBODIMENTS

Figure 18:
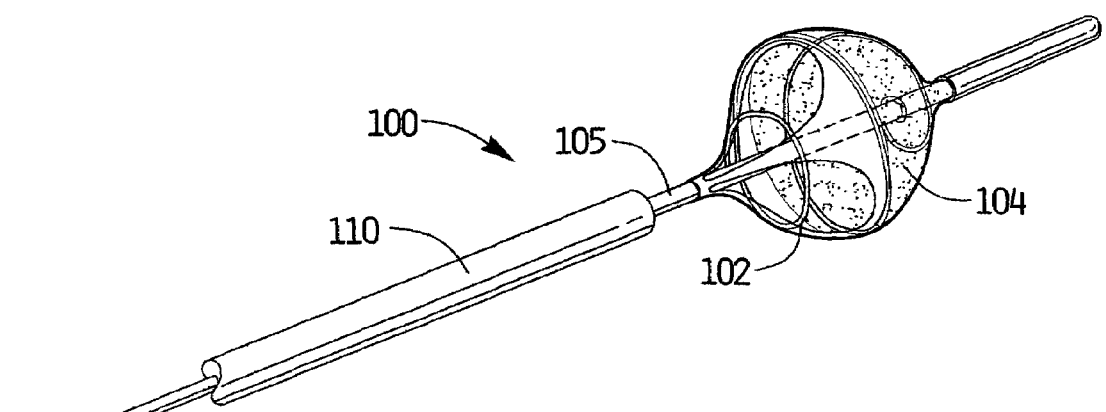
FIGS. 18 and 19 are perspective and side views, respectively, of another alternate embodiment of the distal protection device having a membrane attached to a coiled wire and shown in the expanded position.

Referring now in detail to the drawings where like reference numerals identify similar or like components throughout the several views, several different embodiments for capturing embolic material during surgical procedures.

Turning first to the embodiment of FIGS. 1-5, a catheter 10 has an outer tube 12, a coaxial inner core 14 disposed in the outer tube 12, an inner balloon filter 16 and an outer balloon filter 18. The tube 12 and core 14 are preferably composed of Nitinol, with the core preferably having a platinum wind therearound, however other materials such as stainless steel are also contemplated. The inner balloon filter 16, preferably made of polyurethane, is attached to the catheter 10 at a distal end via ring 29. Balloon 16 has small holes 17 dimensioned for filtering embolic material. The holes 17 are preferably 180 microns, although other dimensions are contemplated. Outer filter balloon 18, also preferably made of PET, is attached at a distal end to catheter 10 via ring 22. As shown, outer filter balloon 18 is external of inner filter balloon 20. Balloon 18 also has a series of holes 19 for filtering embolic material. The holes of the outer balloon 18 are preferably smaller than those of the inner balloon 16 to capture embolic material filtering through the inner balloon 16. In one embodiment, the holes 19 of the outer balloon are 120 microns, although other dimensions are contemplated. Mounting ring 26 supports proximal ends of balloons 16 and 18 and has an inflation port 28 communicating with the space between the balloons.

In use, the space between the balloons 16 and 18 is inflated through inflation port 28, so they are moved to assume the expanded configuration of FIGS. 4 and 5. The inner and outer balloons 16, 18 are preferably attached along a surface so fluid injection to expand the space between the balloons does not enter the balloon and exit through the holes 17, 19.

Thus, embolic material exceeding a certain size carried by the blood through the proximal opening in the balloons is captured in the balloon filters 16, 18, with the blood and smaller particles flowing through the holes 17, 19 in the balloons. As can be appreciated, instead of balloon filters, other inner/outer filtering material with appropriate size holes can be utilized.

FIGS. 8-10 illustrate an alternate embodiment of the distal protection device, designated generally by reference numeral 30. In this embodiment, the blocking membrane is deployed by mechanical actuation of a wire or shaft. More specifically, catheter 31 has a coiled wire 32 attached at a distal end to end wall 37 of tip 34 and at its proximal end to wall 36 by means such as welding. An actuation shaft 38, or alternatively a wire, is slidably positioned within a bore in the catheter 31 and is attached at a distal end 39 to proximal extension 35 of tip 34. A porous membrane 40 is positioned over the coiled wire 32. The membrane 40 can be attached at a proximal end to wall 36 and at a distal end to wall 37 of tip 34. Membrane 40 may also be attached to coiled wire 32. As shown, the membrane 40 fully covers the distal portion of the wire 32 and has enlarged open regions or windows, defined between elongated strips 42, to allow entry of blood.

To deploy the membrane 40 of distal protection device 30 from a low profile insertion position of FIGS. 8 and 9 to an expanded configuration of FIG. 10 to block particles, actuation shaft 38 is pulled proximally (in the direction of the arrow of FIG. 10), thereby pulling tip 34 proximally. Such retraction of tip 34, forces the coiled wire 32 to compress and extend radially outwardly as shown, thereby forcing the membrane 40 radially to a stretched or expanded configuration to block and capture flow of embolic material. The pores in the extended membrane 40 enable blood flow therethrough while capturing embolic material exceeding a predetermined size, i.e. the size of the pores in the membrane. To remove the device 30, actuation shaft 38 is pushed distally to retract the wire 32 and collapse membrane 40.

It should be appreciated that instead of a coiled wire, a tubular braid could be provided with a membrane, e.g. of urethane material, over the braid. The braid would be attached to the catheter and moved between retracted and expanded positions in a similar manner as wire 32. The braided version could alternately be obtained by providing a braided catheter and etching a section of the outer plastic to expose the braid.

FIGS. 6 and 7 illustrate a self expanding distal protection device 50. The self-expansion occurs as a result of blood flow. The distal protection device 50 is an umbrella type device attached to a distal region 51 of guidewire 52. The guidewire 52 is shown with a reduced diameter distal portion 53. The umbrella is in the form of a porous balloon 54, preferably composed of polyurethane, although other materials are also contemplated. A suture loop or ring 56 is attached to a proximal end 51 of the balloon 54 and a suture 58 extends proximally from the suture loop 56. In use, the device is inserted with the balloon 54 in the collapsed low profile position of FIG. 6. When the device 50 is exposed from the catheter or sheath, either by advance of device 50 or retraction of the catheter or sheath, blood flow will expand the balloon 54 to the position shown in FIG. 7 with the mouth 59 open in a proximal direction. The blood will flow through the holes (pores) 55 in the balloon 54, with the embolic material exceeding the size of the pores being captured within the balloon 54. At the end of the procedure, the suture 58 is pulled proximally to flatten and close the mouth 59 of the balloon 54, thus capturing the embolic material inside. The reduced profile of the flattened balloon enables withdrawal of the device through the catheter or sheath.

Being part of a guidewire, in use, the device 50 of FIG. 6 could be placed within the catheter after the guidewire for introducing the catheter is withdrawn. The catheter can then be withdrawn and another catheter, such as a stent delivery catheter could be inserted over the guidewire 52.

Alternate embodiments of a guidewire containing a self-expanding distal protection device are illustrated in FIGS. 12-17. However, rather than expansion by blood flow, the membrane automatically expands when deployed from the catheter as a result of the shape memory or springiness characteristics of the wire underlying the membrane. A 0.018 inch diameter wire can be utilized by way of example, it being understood that wire of other dimensions could be used.

Turning first to the embodiment of FIGS. 12 and 13, distal protection device 70 comprises a membrane or bag 80 and a guidewire 71 having a guidewire extension 72, illustratively of a larger diameter, extending from its distal end. A membrane 80, preferably made of PET, is welded to region 74 of the extension 72. A series of wires 76, preferably composed of shape memory material such as Nitinol, a nickel titanium alloy, extends past the distal end 75 of the guidewire 70 and are welded thereto. Alternately, other materials such as stainless steel with sufficient springiness could be utilized. Four wires are shown but a different number to expand the membrane could be provided. The distal end of the wires 76 are connected to a proximal end 73 of extension 72. Each of the wires curves in the expanded condition as shown. Guidewire 71 is shown by way of example comprising a wound coil around the four wires 76. However, alternately the wires can extend only from the distal end of the guidewire. A flexible mounting ring or band 82 is attached to the proximal end of the membrane 80, at the mouth, and is attached, e.g. welded, to the wires 76. The ring 82 can also be composed of shape memory material to automatically expand when deployed or alternatively of other flexible material to expand when the shape memory wires move to their expanded memorized position. The wires 76 and membrane 80 are retained in a collapsed position within catheter 79 for delivery as illustrated in FIG. 12.

When catheter 79 is pulled proximally in the direction of the arrow, the wires 76 are exposed from the catheter 79, and automatically expand to the memorized position shown in FIG. 13. As they expand they move the membrane 80 from a contracted position to the expanded position of FIG. 13 aided by expansion of band 82. Embolic material flowing through the mouth 84 of the membrane 80 will be captured in the membrane 80, with the blood flowing through the membrane pores. At the end of the procedure, the wires 76 can be fully or partially withdrawn into the catheter 79, or the catheter advanced partially or fully over the wires 76, thus collapsing at least the mouth of the membrane to contain the embolic material therein as the device is withdrawn. A 5-7 French catheter can be used by way of example.

In FIGS. 14-17, three alternate embodiments of wires for attaching the membrane are illustrated. In these embodiments, the wires are also preferably made of shape memory material and form part of the guidewire. They can extend the length of the guidewire as in FIG. 13A or alternatively only extend from the distal end. In these embodiments, the porous membrane is attached only at the end portions of the wires 96, thereby reducing the presence of wires in the flow path. In FIGS. 14 and 15, guidewire 93 of distal protection device 90 has four looped wires 96 extending from region 95 and connected to band or ring 97 of membrane 91 at bend points 98. Membrane 91 is attached at its distal end 94 to guidewire extension 92. Upon deployment from catheter 99, wires 96 move to their memorized position to expand membrane 91. In FIG. 16, shape memory looped wires 96' have more pointed bend points 98' for attachment to the band 97' of membrane 91'. Otherwise, the device 90' is identical to distal protection device 90 of FIG. 15. In the FIG. 17 embodiment, each wire 96" has a curved wire section 92" and a looped section 93" extending from a distal end of the wire section 92" forming a bend point 95" for attachment to the band 97" of membrane 91". These looped wires function in the same manner as in the FIG. 12 embodiment as they are preferably composed of shape memory material so that membrane expansion occurs upon release of the wires from the catheter and collapse of the wires by the catheter closes the membrane to withdraw the device.

Figure 19:
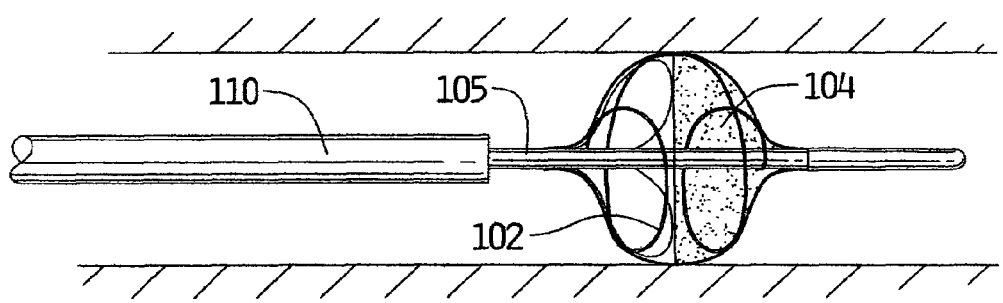
Figure 20:
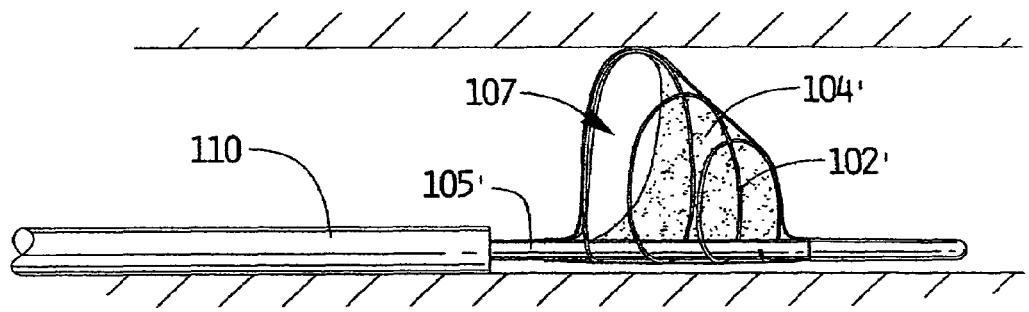
FIG. 20 is a side view of an alternate embodiment of the device of FIG. 18 wherein the coiled wire for deploying the membrane extends on one side of the guidewire.

FIGS. 18 and 19 illustrate an alternate embodiment of the distal protection device of the present invention. Wire 102 of distal protection device 100 expands to a coiled shape as shown to expand a porous membrane 104 into a substantially spherical shape. Wire 102 wraps around the outer surface of the guidewire 105 and forms several loops when expanded. More than one wire could optionally be used. In FIG. 20, wire 102' is offset for positioning on one side of the guidewire 105' such that expansion of the membrane 104' provides a larger region for blood flow and a wider opening in membrane 104' for capture of material. Wire 102' loops around the outer surface of guidewire 105, forming a plurality of loops of progressively increasing diameter toward the proximal end and proximal opening 107 in the membrane 104'. The wires 102, 102' are preferably composed of shape memory material (or springy material) so they expand to the coiled (looped) position when deployed from catheter 110. The wires 102, 102' assume a substantially linear configuration within catheter 110 to maintain a low profile for delivery. When exposed from catheter 110, the wire assumes its coiled shape to expand the membrane 104, 104' to a radially deployed position as shown. Besides a membrane, as with each of the embodiments described herein, other filtering material can be utilized.

In FIGS. 21-24, an alternate embodiment of the distal protection device of the present invention is shown and represented generally by reference numeral 110. A flexible member such as a wire 112 is seated within slot 120 formed in the sidewall of tube 122 and is attached at its distal end 114 to the tube 122 and at its proximal end 116 to slidable tube or shaft 118. A filtering material such as porous membrane 126 covers a region of the tube and the slot 120. In the collapsed position, the wire 112 is preferably fully contained within the tube 122 to reduce the overall insertion profile. In this collapsed position it is in alignment with the slot 120 and the membrane 126 is collapsed around the tube 122. A 0.005 inch diameter wire can be utilized although wires of other dimensions could also be used.

To deploy the device, slidable member such as shaft or tube 118 is advanced in a distal direction (see arrow of FIG. 24) to deploy the wire 112 laterally to bend into a loop extending transversely to a longitudinal axis of the tube 122. End 117 extends proximally and end 119 extends distally. The expanded loop thus lies in a plane at an angle to both the longitudinal axis and transverse axis of the catheter. In other words, the plane of the loop opening would be at an angle (preferably at a slight angle) to the longitudinal and transverse axis of tube 122. The wire 112 would thus extend such that the loop opening is slightly offset from the direction of the longitudinal axis of tube 122 but still open generally in the direction of blood flow. That is, a central longitudinal axis extending through the loop opening would be at an angle with respect to the longitudinal axis of the tube 122.

Consequently, in one embodiment, the plane of the loop opening is perpendicular to the longitudinal axis of the catheter (parallel to the transverse axis) and perpendicular to the direction of blood flow. In other embodiments, rather than perpendicular, the plane of the loop opening is at an angle less than 90 degrees, but preferably greater than about 45 degrees to the longitudinal axis.

The formation of the wire loop stretches the membrane 126 on one side of the catheter to the illustrated expanded configuration of FIGS. 23 and 24 to block the flow of material. This provides additional coverage of the vessel lumen as the catheter can be placed adjacent the internal wall of the vessel with the membrane 126 filling the space above. The windows 127 of membrane 126 provide enlarged openings for blood flow, with the membrane 126 blocking flow of materials exceeding the pore size.

To withdraw the device, the shaft 118 is moved proximally to retract the loop and membrane to the initial low profile insertion position. In a preferred embodiment, the membrane 126 is made of a material that would return automatically from its stretched position to the original collapsed position when the wire is retracted. This passive self-contraction would avoid the need for insertion of a separate device over the membrane to cover it for removal, thus reducing the overall profile of the instrumentation necessary for the procedure. That is, in the preferred embodiment the wire is expanded by active control while the membrane would automatically retract without other assistance.

In another embodiment, the membrane can be attached to wire 112 and move with the wire 112.

Other materials for the embodiments of FIGS. 21-28 can be utilized which as in membrane 126 would be movable between collapsed and deployed positions.

In the embodiment of FIGS. 25 and 26, a flexible member in the form of a wire 131 of distal protection device 130 forms two looped wire regions 132, 134 when expanded so the filtering material such as membrane 136 stretches in two directions. When slidable actuating member such as tube or shaft 138 is advanced distally in the direction of the arrow, the wire 131 bends to extend further through slot 144 in the sidewall of the catheter 142, forming the first looped wire region 132 on one side of catheter 142 and the second looped wire region 134 on the other side of the catheter 142, preferably about 180 degrees apart. This double looped configuration causes membrane 136 to be stretched on opposing sides of the tube 142 to filter materials. As in the embodiment of FIG. 23, the loops are open generally in a direction of blood flow (the plane of the loop opening is substantially transverse to the direction of blood flow and substantially transverse to the longitudinal axis of the device) with blood flowing through windows 137 of membrane 136.

Although shown in axial alignment in FIG. 26, alternatively the wire can be configured so the two looped sections are axially offset as shown in FIG. 28. That is, the loop sections 162, 164 of wire 161 of distal protection device 160 are axially displaced so that loop 162 is positioned distal of loop section 164. As in the previous embodiment, advancement of tube or shaft 172 deploys wire 161 through the slot in the sidewall of tube 174 to assume the looped configuration and stretch porous membrane 176 to the deployed configuration on both sides of tube 174.

In FIG. 27, a double loop configuration of distal protection device 180 is achieved on each side of the tube 192. The flexible member in the form of wire 181 extends through slot 194 of tube 192, forming two loops on each side of tube 192 to stretch membrane (filtering material) 186 when tube or shaft 188 is moved distally. That is, in the expanded configuration, wire 181 extends out of slot 194 to form first loop 185 on a first side of the tube 192, then extends to form second loop 183 on a second opposing side of tube 192, extends upwardly (as viewed in the orientation of FIG. 27) to form third loop 182 on the first side, and then extends to form fourth loop 184 on the second side, after which it extends back through slot 194. As in the other embodiments the loop openings are generally in the direction of blood flow with the plane of the loop openings substantially transverse to the direction of the blood flow. Porous membrane 186 has windows 189.

As noted above, in these embodiments of FIGS. 21-27, the loop opening can be in a plane perpendicular or at an angle less than 90 degrees to the longitudinal axis, but preferably greater than about 45 degrees.

FIG. 29 shows the positioning of the distal protection device of the present invention. By way of example, device 130 of FIG. 26 is shown deployed in the carotid artery "c", it being understood that the other devices described herein can be placed in the same location. The catheter 200 is inserted through the femoral vein "f" as shown in FIG. 24 and advanced to the carotid artery "c". Once positioned at the desired site, catheter 200 is retracted to expose the device 130, or alternately the device 130 is advanced from the catheter 200. Once exposed at the site, the tube is advanced as described above to deploy the wire to the looped configuration to expand membrane 136 to block emboli in the artery.

While the above description contains many specifics, those specifics should not be construed as limitations on the scope of the disclosure, but merely as exemplifications of preferred embodiments thereof. For example, the wire can include radiopaque material for imaging. Those skilled in the art will envision many other possible variations that are within the scope and spirit of the disclosure as defined by the claims appended hereto.

What is claimed is:

1. A distal protection device comprising a catheter having a proximal end portion, a distal end portion, and a cylindrical wall extending from the proximal end portion to the distal end portion along a longitudinal axis and having a sidewall formed therein and a slot formed in a portion of the sidewall, the slot extending parallel to the longitudinal axis and positioned proximal of a distal end of the catheter to form an opening in the sidewall, a single flexible member forming first and second loop openings, the flexible member movable from a first retracted position wherein a portion lies within the opening in the sidewall to a second looped position extending laterally with respect to the catheter and through the opening in the sidewall such that the first loop opening extends substantially in a direction of blood flow as the first loop opening lies in a plane substantially parallel to a transverse axis of the catheter and the second loop opening extends substantially in a direction of blood flow as the second loop opening lies in a plane substantially parallel to a transverse axis of the catheter, and filtering material movable from a collapsed position to an expanded position in response to movement of the flexible member, the filtering material allowing blood flow therethrough while capturing embolic material dislodged by a treatment device.

2. The device of claim 1, wherein the portion of the flexible member is contained within the catheter in the first position so the cross sectional dimension of the catheter at a portion containing the flexible member does not exceed other cross-sectional dimensions of the catheter.

3. The device of claim 1, wherein in the looped position, the first and second loop openings are radially spaced.

4. The device of claim 3, wherein the first and second loop openings extend in opposite directions with respect to the catheter so in the looped position the loops are approximately 180 degrees apart.

5. The device of claim 3, wherein the first and second loop openings are axially offset so that one loop opening is positioned distally of the other loop opening along the longitudinal axis.

6. The device of claim 1, wherein the first and second loop openings are axially offset so that one loop is positioned distally of the other loop.

7. The device of claim 1, further comprising an actuating member movable from a first position to a second position to move the flexible member into the looped position.

8. The device of claim 1, wherein the filtering material automatically moves back from the expanded position to the collapsed position upon movement of the actuating member back to the first position.

9. The device of claim 1, wherein the first and second loop openings are axially offset so that one loop opening is positioned distally of the other loop opening along the longitudinal axis.

10. The device of claim 1, wherein a central portion of the first loop opening and a central portion of the second loop opening are radially spaced from the longitudinal axis.

11. A distal protection device comprising a catheter having a slot extending parallel to a longitudinal axis of the device and forming an opening in a portion of a sidewall spaced proximally from a distal end of the sidewall, a single flexible wire having a portion positioned within the opening of the catheter in a first retracted position and movable from a first position having a lower profile for insertion of the catheter to a second position extending laterally from the catheter and through the sidewall, in the second position the single wire forms first and second loops extending laterally such that a first end of the wire extends in a proximal direction and a second end of the wire extends in a distal direction with the first and second loops therebetween each having an opening extending in a proximal to distal direction, and filtering material disposed over at least a portion of the wire and movable from a collapsed position to an expanded position in response to movement of the wire, the filtering material in the expanded position allowing blood flow therethrough while capturing embolic material dislodged by a treatment device.

12. The device of claim 11, further comprising an actuating member for moving the wire into the second position.

13. The device of claim 11, wherein the first and second loops are axially offset so that one loop is positioned distally of the other loop along the longitudinal axis.

14. The device of claim 11, wherein a central portion of the opening in the first loop and a central portion of the opening in the second loop are radially spaced from the longitudinal axis.

* * * * *